United States Patent [19]

Hattler

[11] Patent Number: 4,986,809

[45] Date of Patent: * Jan. 22, 1991

[54] PERCUTANEOUS OXYGENATOR

[76] Inventor: Brack G. Hattler, 5226 Westminster Pl., Pittsburgh, Pa. 15232

[*] Notice: The portion of the term of this patent subsequent to Mar. 27, 2007 has been disclaimed.

[21] Appl. No.: 485,299

[22] Filed: Feb. 26, 1990

Related U.S. Application Data

[63] Continuation-in-part of Ser. No. 338,581, Apr. 17, 1989, Pat. No. 4,911,689.

[51] Int. Cl.$^5$ .............................................. A61M 37/00
[52] U.S. Cl. ........................................ 604/26; 623/12; 623/1; 604/4; 604/49
[58] Field of Search ............. 128/DIG. 3; 604/23–26, 604/48, 49, 52–53, 47, 43; 422/45, 46, 48; 628/1, 12, 9, 66; 261/DIG. 28, 122

[56] References Cited

U.S. PATENT DOCUMENTS

| | | | |
|---|---|---|---|
| 3,505,686 | 4/1970 | Bodell | 3/1 |
| 4,159,720 | 7/1979 | Burton | 128/260 |
| 4,346,006 | 8/1982 | Kopp et al. | 210/321.4 |
| 4,583,969 | 4/1986 | Mortensen | 604/49 |
| 4,631,053 | 12/1986 | Taheri | 604/49 |
| 4,743,250 | 5/1988 | Kitagawa et al. | 623/1 |
| 4,850,958 | 7/1989 | Berry et al. | 604/53 |
| 4,911,689 | 3/1990 | Hattler | 604/26 |

Primary Examiner—C. Fred Rosenbaum
Assistant Examiner—Kathleen A. Daley
Attorney, Agent, or Firm—Dorr, Carson, Sloan & Peterson

[57] ABSTRACT

A percutaneous oxygenator has a Y-shaped tubular connector and a number of hollow, gas-permeable fibers. One end of each fiber is located in the first upper arm of the connector. The other end of each fiber is located in the other upper arm of the connector, with each fiber forming a loop extending out of the lower opening of the connector. To guide insertion of the device into a patient's vein, and to provide structural support for the fiber loops, a support member extends downward from the connector with an aperture at is distal end. Each of the fiber loops pass through this aperture. The device is inserted through a single small incision into the patient's venous system. An oxygen supply is attached to one of the upper arms of the connector and flows through the length of the fiber loops. Oxygen and carbon dioxide diffuse across the fiber walls between the blood and the interior of the fiber tubes. In one alternative embodiment, a tip having an interior cavity is secured to the lower end of the support member. Each of the fiber loops is bisected and in fluid communication with the mixing chamber provided by the interior cavity of the tip. In another alternative embodiment, the support member is a hollow tube. Oxygen is supplied through the support member into the mixing chamber inside the tip, and returns to the connector through both arms of the fiber loops.

27 Claims, 5 Drawing Sheets

PERCUTANEOUS OXYGENATOR

RELATED APPLICATION

This application is a continuation-in-part of the applicant's co-pending U.S. patent application Ser. No. 07/338,581, entitled "Percutaneous Oxygenator", filed on Apr. 17, 1989 now U.S. Pat. No. 4,911,689.

BACKGROUND OF THE INVENTION

1. Field of the Invention

The present invention relates generally to the field of oxygenators used to increase the oxygen level in a patient's blood. More particularly, the present invention involves a percutaneous oxygenator that can be positioned within a patient's body, as for example in the inferior vena cava, superior vena cava, the right atrium of the heart, or any combination thereof.

2. Statement of the Problem

Many types of blood oxygenators are well known in the art. For example, during open heart surgery, the patient is interconnected with an external oxygenator, commonly known as a heart-lung machine, which introduces oxygen into the blood system. Most types of oxygenators use a gas-permeable membrane. Blood flows along one side of the membrane, and oxygen is supplied to the other side of the membrane. Given a sufficient pressure gradient between the oxygen supply and the blood, the oxygen will diffuse through the membrane and into the blood. In addition, carbon dioxide will tend to diffuse from the blood into the membrane.

In other situations, a smaller, implantable oxygenator may be sufficient to adequately supplement the patient's cardiopulmonary function by marginally increasing the oxygen content of the patient's blood. For example, patients suffering from emphysema, pneumonia, congestive heart failure, or other chronic lung disease often have blood oxygen partial pressures of approximately 40 torr. A relatively small increase of 10% to 20% is generally sufficient to adequately maintain the patient. This is a particularly desirable alternative in that it avoids the need to intubate the patient in such cases. In addition, temporary use of this type of oxygenator is sufficient in many cases to tide the patient over an acute respiratory insult. Placing such patients on a conventional respirator is often the beginning of a progressive downhill spiral by damaging the patient's pulmonary tree and thereby causing greater dependence on the respirator.

A number of devices and processes have been invented in the past incorporating this basic technology, including the following:

| Inventor | Patent No. | Issue Date |
|---|---|---|
| Bodell | 3,505,686 | Apr. 14, 1970 |
| Burton | 4,159,720 | July 3, 1979 |
| Kopp, et al. | 4,346,006 | Aug. 24, 1982 |
| Mortensen | 4,583,969 | Apr. 22, 1986 |
| Taheri | 4,631,053 | Dec. 23, 1986 |
| Kitagawa, et al. | 4,743,250 | May 10, 1988 |

The Bodell patent demonstrates the general concept of using gas permeable fibers to boost the oxygen level of blood. FIGS. 6 and 10 show two variations of this device intended for use inside the body of the patient. In the implantable embodiment of the Bodell device, a tubular casing serves as a shunt either from the pulmonary artery to the left atrium of the heart (FIG. 6), or more generally between an artery and a vein (FIG. 10). A multitude of parallel-connected capillary tubes are used to oxygenate and/or purify the blood circulating through the casing.

FIGS. 3–5 of the Mortensen patent show a transvenous oxygenator made of a plurality of small diameter gas permeable tubes 32 connected to headers 34 and 36 at each end. However, the specific device disclosed by Mortensen has a significant disadvantage in that two incisions are required. The insertion process is also rather complex.

The Taheri patent discloses a transvenous oxygenator having a single membrane 16 through which oxygen diffuses. The membrane is disposed within a sheath 18 and both are supported by a flexible wire 20.

The remaining references are of lesser pertinence.

3. Solution to the Problem

None of the prior art references uncovered in the search show oxygenation by means of a number of parallel loops of hollow tubes supported by a wire stylet that is inserted through a single small incision. Furthermore the unique Y-shaped connector used in the present invention is also not disclosed in any of these references.

SUMMARY OF THE INVENTION

This invention provides a percutaneous oxygenator having a Y-shaped tubular connector and a plurality of hollow, gas-permeable fibers. One end of each fiber is located in the first upper arm of the connector. The other end of each fiber is located in the other upper arm of the connector, with each fiber forming a loop extending out of the lower opening of the connector. To guide insertion of the device into a patient's vein, and to provide structural support for the fiber loops, an elongated support member extends downward from the connector with an aperture at its distal end. Each of the fiber loops pass through this aperture. The device is inserted through a single small incision into a vein, and once in place occupies the superior vena cava, inferior vena cava, right atrium, or some combination of these areas in the patient. An oxygen supply is attached to one of the upper arms of the connector. Oxygen flows through the hollow fibers and diffuses through the fiber wall into the blood. Carbon dioxide diffuses in the opposite direction across the fiber wall from the blood into the interior of the fiber loops. This carbon dioxide and any remaining oxygen exits the fibers and is vented to the atmosphere at the second upper arm of the connector. The fiber loops can be crimped and/or twisted into a helical arrangement to enhance gas exchange.

Alternatively, a tip housing a hollow mixing chamber can be affixed to the distal end of the support member in place of the aperture discussed above. Each of the fiber loops is bisected and the ends are sealed in fluid communication with the mixing chamber to create a complete path for circulation of gases through both arms of the fiber loops and the mixing chamber.

In another alternative embodiment, the support member is a hollow tube that is used to supply oxygen to the chamber inside the tip. In this configuration, oxygen flows through the support member, into the mixing chamber inside the tip, and returns to the connector through both arms of the fiber loops.

A primary object of the present invention is to provide an oxygenator that can be easily implanted into a patient through a single incision, to boost the oxygen level and to remove carbon dioxide from the patient's blood.

Another object of the present invention is provide a disposable oxygenator that can be relatively simply and inexpensively produced and then discarded after use.

Yet another object of the present invention is to provide a compact oxygenator having a large surface area for diffusion of oxygen in comparison to its volume, thereby minimizing trauma to the patient and also minimizing obstruction to the flow of blood.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figures 1, 3:
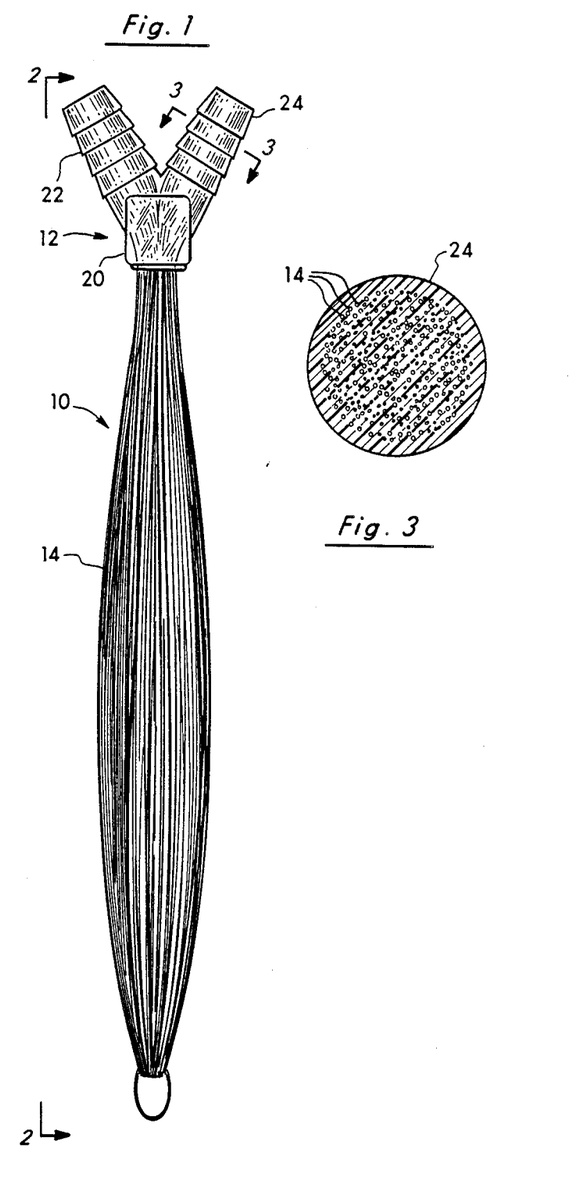
FIG. 1 is a perspective view of oxygenator.
FIG. 3 is a cross-sectional view of one upper arm of the Y-shaped connector of the oxygenator.
Figure 2:
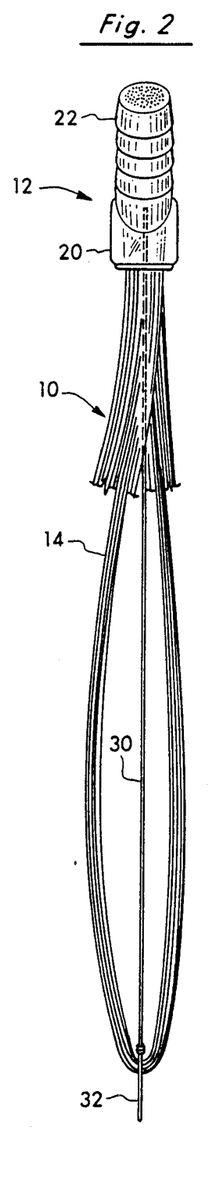
FIG. 2 is a partial side view of the oxygenator showing, as an example, the manner in which a few of the fibers loop through the aperture at the end of the support member.
Figure 4:
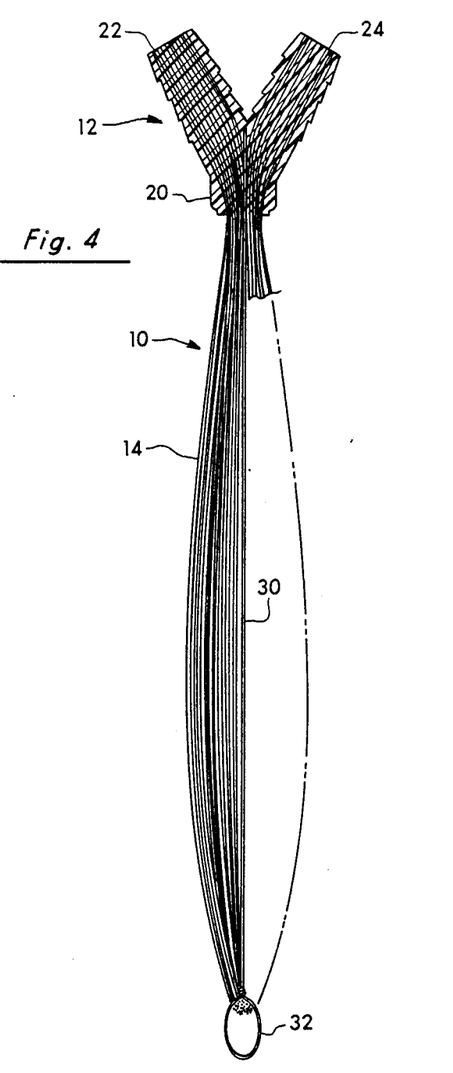
FIG. 4 is a vertical cross-sectional view of the oxygenator, corresponding to FIG. 1.

Turning to FIG. 1, the oxygenator 10 is shown as having a Y-shaped tubular connector 12 and a multitude of parallel loops of hollow, gas-permeable fibers 14. The Y-shaped connector 12 has a tubular base 20 and two tubular upper arms 22 and 24 extending from the upper end of the tubular base 20. External openings exist at the distal ends of the base and both upper arms of the connector. One end of each fiber 14 is located in the first upper arm 22, in fluid communication with the external opening at the end of this upper arm of the connector 12. The body of each fiber 14 forms a loop extending from the first upper arm 22 downward out of the external opening at the bottom of the tubular base 20, and then upward back through the tubular base 20 and into the second upper arm 24 of the connector. The second end of each fiber 14 is located in fluid communication with external opening at the end of the second upper arm 24. FIG. 2 more clearly shows the loops formed by each fiber 14. A corresponding partial cross-sectional view of this device is shown in FIG. 4.

Figure 5:
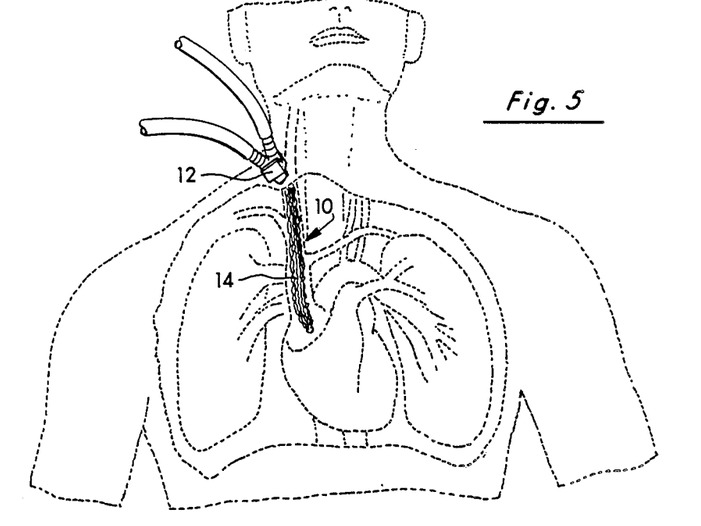
FIG. 5 is a cross-sectional view of a portion of the patient's body showing the oxygenator implanted through the right internal jugular vein into the superior vena cava.

The fiber loops of the device are implanted in the venous system of the patient through a single small incision. For example, FIG. 5 shows the device implanted through the right interior jugular vein into the superior vena cava of a patient. For maximum effectiveness, the fiber loops are fully inserted through the incision up to the level of the base 20 of the connector 12. Insertion of the fiber loops can be aided by using a conventional introducer similar to the type presently employed to insert a cardiac pacemaker. The connector 12 remains largely outside incision. Optionally, a flexible plastic cuff (not shown) extending laterally outward from the base 20 of the connector 12 covers the area surrounding the incision.

As shown in FIG. 1, a multitude of fiber loops 14 extend from the base of the connector 12 to form a compact bundle having a large total surface area for diffusion of oxygen into the blood stream, and diffusion of carbon dioxide out of the blood stream. Any of a variety of flexible, hollow, gas-permeable fibers currently available on the market, such Mitsubishi KPF190M polypropylene fibers, are suitable for this purpose. To provide a true ideal membrane, the polypropylene fibers should be coated with silicone rubber and bonded with a non-thrombogenic component.

After the device has been implanted, an oxygen supply is attached to either one of the upper arms 22 or 24 of the connector 12. Oxygen flows into the ends of the fibers 14 in the attached upper arm of the connector, and through the fiber loops. Oxygen diffuses outward through the walls of the fiber loops into the surrounding blood stream. Carbon dioxide diffuses inward from the blood stream through the walls of the fiber loops into the interior of the fibers. This carbon dioxide and any remaining oxygen in the fibers are vented to the atmosphere at the distal end of the fibers through the external opening at the second, unattached upper arm of the connector 12. Alternatively, negative pressurization can be applied by means of a conventional vacuum pump to the second upper arm of the connector to enhance gas flow through the fiber loops.

In the preferred embodiment of the present invention, a sealing material is introduced into the upper arms 22 and 24 of the connector 12 to fill the voids remaining between the fibers 14, without plugging the ends of the these fibers. This ensures that all of the oxygen provided by the oxygen supply flows through the fibers, rather than leaking directly to the atmosphere through the connector. Use of this sealing material is shown in the cross-sectional view of an upper arm of the connector in FIG. 3.

As shown in FIGS. 2 and 4, an elongated support member 30 can be employed to provide structural support and to guide the fiber loops during the insertion process. This support member is secured at one end to the connector 12. The distal end of the support member has an aperture 32 through which all of the fiber loops 14 pass. In the preferred embodiment of the present invention shown in the figures, this support member is a wire 30 having a loop 32 at its distal end. The upper end of this wire 30 extends through the opening in the bottom of the connector 12, where it is secured by the sealing material which fills the upper portions of the interior of the connector 12. The length of the wire, from the bottom of the connector 12 to the top of the loop 32, is slightly less than one half of the peripheral length of the fiber loops 14. This causes the fiber loops to form elongated loops that can be more readily inserted through a small incision into a vein.

The device is readily implanted and removed through a single small incision. This permits the device to be quickly implanted and used on an intermittent basis in response to changes in the patient's respiratory status. The ability to repeatedly insert and remove the devise is somewhat akin to the intermittency of treatment by dialysis for acute renal failure. Thus, this form of therapy might be termed "respiratory dialysis" for patients in respiratory failure. Although in raising the comparison with renal dialysis, the physiology of these two forms of therapy are obvious not comparable.

Figure 6:
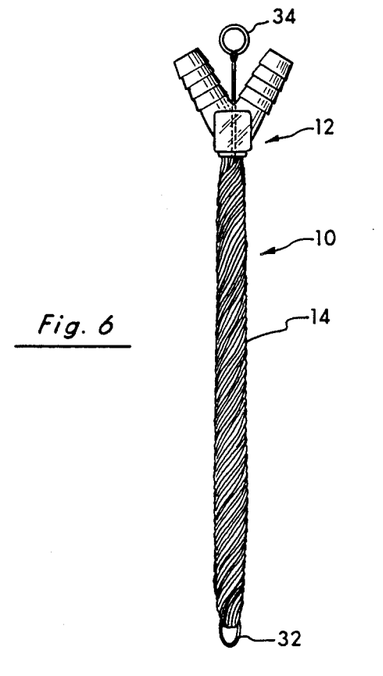
FIG. 6 is a perspective view of an alternative embodiment of the present invention in which the fiber loops are helically twisted about one another to form a cork screw arrangement.

FIG. 6 shows an alternative embodiment of the present invention in which the fiber loops 14 are helically wound around the support member 30 in a cork screw arrangement. This increases the length and surface area of the fibers and thereby increases diffusion of oxygen and carbon dioxide across the walls of the fiber loops. The resulting complex surface shape also increases turbulence in the blood flow around the fiber loops, which further increases gas exchange across the walls of the fiber loops.

FIG. 6 also illustrates use of a rotatable support member to control the degree of helical winding of the fiber loops 14. The upper end of the support member 30 shown in the previous figures is firmly secured to the connector 12. In FIG. 6, the upper end 34 of the support member 30 extends through the connector 12, and can be manually rotated with respect to the connector 12 about the longitudinal axis of the support member 30. The fiber loops 14 extending through the aperture 32 at the bottom of the support member 30 are therefore helically wound (or unwound) by rotation of the upper end of support member 34. Prior to insertion of the device, the support member 30 is rotated to tightly wind the fiber loops 14 into a smaller, more compact volume allowing easier insertion into the vein. After the device is positioned in the vein, the support member is then rotated in the opposite direction to partially or completely unwind and unfurl the fiber loops, allowing circulation of blood between the individual fiber loops.

Figure 7:
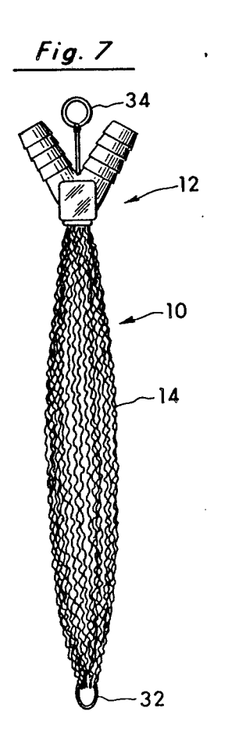
FIG. 7 is a perspective view of another alternative embodiment of the present invention in which the fiber loops have been crimped at a number of points along their peripheral length.
Figure 8:
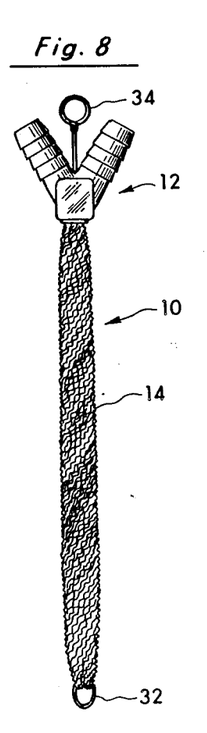
FIG. 8 is a perspective view of another alternative embodiment of the present invention in which the fiber loops have been both crimped, as shown in FIG. 7, and twisted into a cork screw arrangement, as shown in FIG. 6.

FIG. 7 shows another alternative embodiment in which the individual fiber loops 14 have been crimped at a number of points along their peripheral lengths. This increases the length of each fiber loop and increases circulation and turbulence of the blood flow, thereby increasing gas exchange across the walls of the fiber tubes 14. FIG. 8 shows the combination of helical winding from FIG. 6, with crimping of the fiber loops form FIG. 7.

Figure 9:
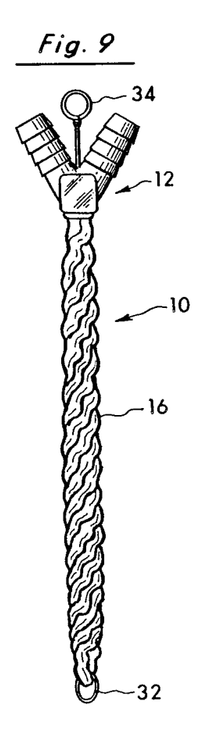
FIG. 9 is a perspective view of yet another alternative embodiment using a single large-bore hollow fiber in place of the multitude of smaller fibers employed in the previous embodiments.

FIG. 9 shows yet another alternative embodiment in which a single large-bore tube is crimped and helically wound around the support member, in place of the multitude of smaller fibers shown in the previous drawings.

In another alternative embodiment not shown in the figures, the support member 30 is omitted and the fiber loops 14 are housed within a conventional French catheter. Following insertion of the catheter and fiber loops 14 into the patient, blood circulates through the catheter and around the fiber loops within the catheter.

It should be noted that the device described above can also be used to administer anesthetic gases or other medications directly into the patient's blood system. For this purpose, a mixture of oxygen and anesthetic gases flow through the fiber loops of the device and diffuse into the patient's blood stream.

Figures 10, 11:
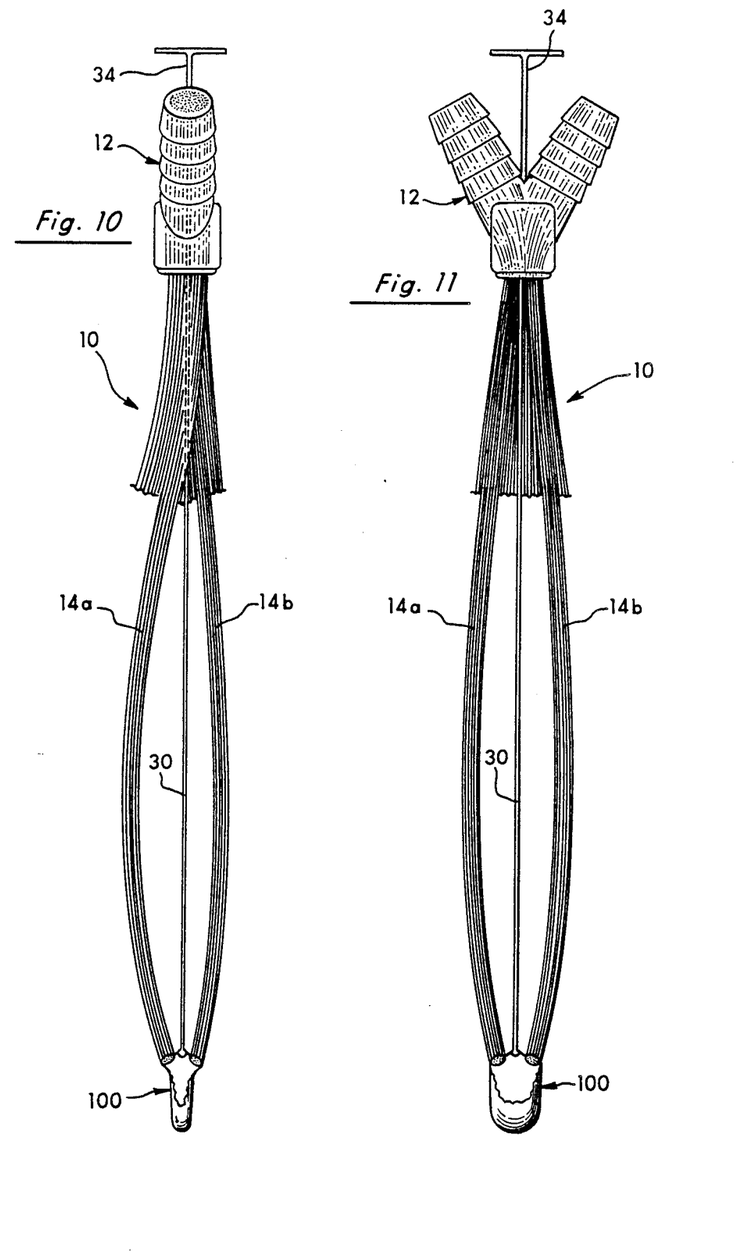
FIG. 10 is a partial side view of another alternative embodiment of the present invention in which a tip housing a mixing chamber is attached at the end of the support member.
FIG. 11 is a partial front view of the alternative embodiment shown in FIG. 10.

FIGS. 10 and 11 show another alternative embodiment in which the aperture or loop at the distal end of the support member 30 has been replaced by a tip 100 having an internal cavity. Each of the fiber loops is bisected at its distal point into two arms 14a and 14b. The resulting ends of the fibers are sealed in fluid communication with the internal cavity of the tip 100. Thus, gases flowing down one arm 14a of the fibers enter the tip 100, are mixed within its internal cavity of the tip 100, and then flow upward through the other arm 14b of the fibers. The tip can be molded from plastic or rubber around the ends of the fiber arms to prevent the escape of gases at the junction between the fiber ends and the tip. The tip can also be shaped with a tapered contoured to ease insertion of the device through an incision. As shown in FIGS. 10 and 11, the fibers are typically connected to the upper sections of the tip. This configuration minimizes bending stresses placed on the fibers, and also minimizes stresses placed on the fibers during the insertion process.

As previously mentioned, the support member 30 may be rotatable with respect to the Y-shaped connector 12. In this embodiment, the tip 100 is generally secured to the distal end of the support member 30, so that the tip 100 and the distal ends of the fiber arms 14a and 14b rotate with the support member 30. This causes the fiber arms 14a and 14b to become helically wound about the support member 30, in a manner similar to that shown in FIG. 6.

In another alternative embodiment, the support member 30 is a hollow tube extending through the Y-shaped connector 12 to the mixing chamber in the interior of the tip 100. The upper end of the connector extending through the connector 12 is placed in fluid communication with a source of oxygen and/or other medication. Both of the upper arms of the connector 12 are either vented to the atmosphere, or else subjected to negative pressurization. The result is a flow of oxygen from the source into the upper end of the support member 30, through the length of the support member 30 into the mixing chamber inside the tip 100, and upward through both sets of fiber arms 14a and 14b to exit through the upper arms of the connector 12.

The above disclosure sets forth a number of embodiments of the present invention. Other arrangements or embodiments, not precisely set forth, could be practiced under the teachings of the present invention and as set forth in the following claims.

I claim:

1. A percutaneous oxygenator comprising:
   (a) a tubular connector having a lower opening and an upper portion dividing to form two passageways in fluid communication with said lower opening, both of said passageways having a separate exterior opening; and
   (b) a first group of a number of hollow, gas-permeable fibers, each fiber having two ends, the first end of each fiber located in the first passageway of said connector in fluid communication with the exterior opening of said first passageway, said fibers extending downward through said lower opening with the second end of each fiber located a predetermined distance below said lower opening;

(c) a second group of a number of hollow, gas-permeable fibers, each fiber having two ends, the first end of each fiber located in the second passageway of said connector in fluid communication with the exterior opening of said second passageway, said fibers extending downward through said lower opening with the second end of each fiber located a predetermined distance below said lower opening;

(d) a tip member having an interior cavity in fluid communication with the second ends of said first group of fibers and with the second ends of said second group of fibers.

2. The percutaneous oxygenator of claim 1 wherein said fibers are comprised of microporous polypropylene.

3. The percutaneous oxygenator of claim 2 wherein said polypropylene fibers are coated with a thin layer of silicone rubber to which is bonded a non-thrombogenic surface.

4. The percutaneous oxygenator of claim 1 further comprising sealing material filling any voids inside said connector passageways between said fibers, without plugging the first ends of said fibers.

5. The percutaneous oxygenator of claim 1 wherein the connector has a Y-shaped configuration.

6. The percutaneous oxygenator of claim 1 wherein said fibers are twisted into a helical arrangement.

7. The percutaneous oxygenator of claim 1 wherein said fibers are crimped at a number of points along their peripheral length.

8. The percutaneous oxygenator of claim 1 further comprising an elongated support member extending from said connector adapted to support said fiber loops with respect to said connector.

9. The percutaneous oxygenator of claim 8 wherein said support member comprises a wire extending downward from said base attached to said tip member.

10. The percutaneous oxygenator of claim 8 wherein said support member is rotatable about its longitudinal axis with respect to said connector.

11. A percutaneous oxygenator comprising:
(a) a connector having
  (i) a tubular base with a lower end with an exterior opening and an upper end, and
  (ii) two tubular arms, each arm extending from the upper end of said base, with an exterior opening at its distal end; and
(b) a first group of a number of hollow, gas-permeable fibers, each fiber having two ends, the first end of each fiber extending upward through the lower end of said base and into the first arm of said connector, with the second end of each fiber located a predetermined distance below the lower end of said base;
(c) a second group of a number of hollow, gas-permeable fibers, each fiber having two ends, the first end of each fiber extending upward through the lower end of said base and into the second arm of said connector, with the second end of each fiber located a predetermined distance below the lower end of said base;
(d) a tip member having an interior cavity in fluid communication with the second ends of said first group of fibers and with the second ends of said second group of fibers.

12. The percutaneous oxygenator of claim 11 wherein said fibers are comprised of microporous polypropylene.

13. The percutaneous oxygenator of claim 11 wherein said polypropylene fibers are coated with a thin layer of silicone rubber to which is bonded a non-thrombogenic surface.

14. The percutaneous oxygenator of claim 11 further comprising sealing material filling any voids inside at least one of said tubular arms between said fibers, without plugging the first ends of said fibers.

15. The percutaneous oxygenator of claim 11 wherein the connector has a Y-shaped configuration.

16. The percutaneous oxygenator of claim 11 further comprising a support member extending from said connector adapted to support said fiber loops with respect to said connector.

17. The percutaneous oxygenator of claim 11 wherein said support member comprises a wire extending downward from said base attached to said tip member.

18. The percutaneous oxygenator of claim 16 wherein said support member is rotatable about its longitudinal axis with respect to said connector.

19. The percutaneous oxygenator of claim 11 wherein said fibers are twisted into a helical arrangement.

20. The percutaneous oxygenator of claim 11 wherein said fibers are crimped at a number of points along their peripheral length.

21. A percutaneous oxygenator comprising:
(a) a Y-shaped tubular connector having a tubular base with an exterior opening at its lower end; and two tubular arms, each arm extending from the upper end of said base, with an exterior opening at its distal end; and
(b) a first set of hollow, gas-permeable fibers, each fiber having two ends, the first end of each fiber extending upward through the lower end of said base and into the first arm of said connector, with the second end of each fiber extending a predetermined distance below the lower end of said base;
(c) a second set of hollow, gas-permeable fibers, each fiber having two ends, the first end of each fiber extending upward through the lower end of said base and into the second arm of said connector, with the second end of each fiber extending a predetermined distance below the lower end of said base;
(d) an elongated support member rotatably attached to said connector;
(e) a tip member secured to the distal end of said support member, said tip member having an interior cavity in fluid communication with the second ends of said first set of fibers and with the second ends of said second set of fibers.

22. The percutaneous oxygenator of claim 21 wherein said support member comprises a wire, one end of which passes through said connector, the other distal end of which is secured to said tip member.

23. A percutaneous oxygenator comprising:
(a) a tubular connector having a tubular base with an exterior opening at its lower end; and two tubular arms, each arm extending from the upper end of said base with an exterior opening at its distal end;
(b) a first set of hollow, gas-permeable fibers, each fiber having two ends, the first end of each fiber extending upward through the lower end of said base and into the first arm of said connector, with the second end of each fiber located a predetermined distance below the base of said connector;

(c) a second set of hollow, gas-permeable fibers, each fiber having two ends, the first end of each fiber extending upward through the lower end of said base and into the second arm of said connector, with the second end of each fiber located a predetermined distance below the base of said connector;

(d) sealing material filling any voids inside at least one of said tubular arms and around the first ends of said fibers, to ensure that oxygen introduced into the external opening of said tubular arm flows only into said fibers; and (e) a tip member having an interior cavity in fluid communication with the second ends of said first group of fibers and with the second ends of said second group of fibers.

24. The percutaneous oxygenator of claim 23 further comprising an elongated support member extending downward from said connector, with its distal end secured to said tip member.

25. The percutaneous oxygenator of claim 23 wherein the connector has a Y-shaped configuration.

26. The percutaneous oxygenator of claim 23 wherein said fibers are comprised of microporous polypropylene.

27. The percutaneous oxygenator of claim 26 wherein said polypropylene fibers are coated with a thin layer of silicone rubber to which is bonded a non-thrombogenic surface.

* * * * *

UNITED STATES PATENT AND TRADEMARK OFFICE
Certificate

Patent No. 4,986,809            Patented: Jan. 22, 1991

On petition requesting issuance of a certificate for correction of inventorship pursuant to 35 U.S.C. 256, it has been found that the above-identified patent, through error and without any deceptive intent, improperly sets forth the inventorship.

Accordingly, it is hereby certified that the correct inventorship of this patent is: Brack G. Hattler and Gary D. Reeder Signed and Sealed this Seventh Day of May, 1991.

C. FRED ROSENBAUM

*S. P. E.*
*Art Unit 336*